United States Patent
Remarchuk et al.

(10) Patent No.: US 11,834,438 B2
(45) Date of Patent: Dec. 5, 2023

(54) PROCESS FOR THE PREPARATION OF PYRIMIDINYL-4-AMINOPYRAZOLE COMPOUNDS

(71) Applicant: DENALI THERAPEUTICS INC., South San Francisco, CA (US)

(72) Inventors: Travis Remarchuk, South San Francisco, CA (US); Anantha Sudhakar, South San Francisco, CA (US)

(73) Assignee: DENALI THERAPEUTICS INC., South San Francisco, CA (US)

( * ) Notice: Subject to any disclaimer, the term of this patent is extended or adjusted under 35 U.S.C. 154(b) by 0 days.

(21) Appl. No.: 16/955,717

(22) PCT Filed: Dec. 19, 2018

(86) PCT No.: PCT/US2018/066595
§ 371 (c)(1),
(2) Date: Jun. 18, 2020

(87) PCT Pub. No.: WO2019/126383
PCT Pub. Date: Jun. 27, 2019

(65) Prior Publication Data
US 2021/0009566 A1    Jan. 14, 2021

Related U.S. Application Data

(60) Provisional application No. 62/608,398, filed on Dec. 20, 2017.

(51) Int. Cl.
*C07D 403/12*    (2006.01)
(52) U.S. Cl.
CPC .................... *C07D 403/12* (2013.01)
(58) Field of Classification Search
CPC .................................................... C07D 403/12
See application file for complete search history.

(56) References Cited

U.S. PATENT DOCUMENTS

| | | | |
|---|---|---|---|
| 8,354,420 B2 | 1/2013 | Baker-Glenn et al. | |
| 8,569,281 B2 | 10/2013 | Chan et al. | |
| 8,791,130 B2 | 7/2014 | Baker-Glenn et al. | |
| 8,796,296 B2 | 8/2014 | Baker-Glenn et al. | |
| 8,802,674 B2 | 8/2014 | Baker-Glenn et al. | |
| 8,809,331 B2 | 8/2014 | Baker-Glenn et al. | |
| 8,815,882 B2 | 8/2014 | Baker-Glenn et al. | |
| 9,145,402 B2 | 9/2015 | Baker-Glenn et al. | |
| 9,212,173 B2 | 12/2015 | Baker-Glenn et al. | |
| 9,212,186 B2 | 12/2015 | Baker-Glenn et al. | |
| 9,932,325 B2 | 4/2018 | Estrada et al. | |
| 11,111,235 B2 | 9/2021 | De Vicente Fidalgo et al. | |
| 2015/0250790 A1 | 9/2015 | Parikh et al. | |
| 2017/0362206 A1 | 12/2017 | Estrada et al. | |

FOREIGN PATENT DOCUMENTS

| | | |
|---|---|---|
| WO | 2011151360 A1 | 12/2011 |
| WO | 2012062783 A1 | 5/2012 |
| WO | 2013079493 A1 | 6/2013 |
| WO | 2013079494 A1 | 6/2013 |
| WO | 2013079495 A1 | 6/2013 |
| WO | 2013079496 A1 | 6/2013 |
| WO | 2013079505 A1 | 6/2013 |
| WO | 2013164321 A1 | 11/2013 |
| WO | 2013164323 A1 | 11/2013 |
| WO | 2014026243 A1 | 2/2014 |
| WO | 2017019804 A2 | 2/2017 |
| WO | 2017087905 A1 | 5/2017 |
| WO | 2017156493 A1 | 9/2017 |
| WO | 2017218843 A1 | 12/2017 |
| WO | 2018217946 A1 | 11/2018 |
| WO | 2019104086 A1 | 5/2019 |
| WO | 2020210684 A1 | 10/2020 |

OTHER PUBLICATIONS

Supplementary European Search Report in EP 18892459.1 dated Jul. 20, 2021, 12 pages.
International Search Report in PCT/US2018/066595 dated May 7, 2019, 3 pages.

(Continued)

*Primary Examiner* — Brian E McDowell
(74) *Attorney, Agent, or Firm* — McCarter & English, LLP; Steven G. Davis; Xin Zhang

(57) ABSTRACT

The present disclosure relates to methods of making LRRK2-inhibiting, pyrimidinyl-4-aminopyrazole compounds and intermediates of formulae I and IV: The compounds are useful as LRRK2 inhibitors in the treatment of LRRK2 mediated diseases, and as intermediates for their manufacture.

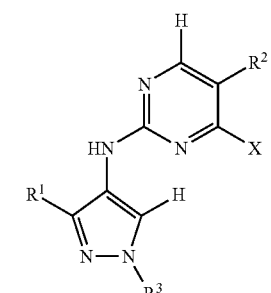

I

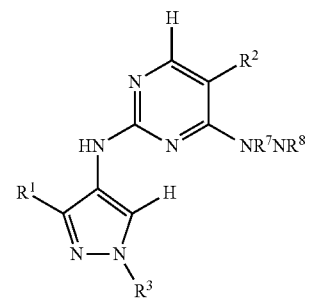

IV

6 Claims, No Drawings

(56) References Cited

OTHER PUBLICATIONS

Examination Report in Indian patent application No. 202017028562 dated Jan. 5, 2022, 6 pages.
Chan, et al., "Discovery of a Highly Selective, Brain-Penetrant Aminopyrazole LRRK2 Inhibitor", ACS Medicinal Chemistry Letters 4, 85-90 (2013).
Chen, et al., "Discovery of Selective LRRK2 Inhibitors Guided by Computational Analysis and Molecular Modeling", Journal of Medicinal Chemistry 55, 5536-5545 (2012).
Christensen, et al., "Development of LRRK2 Inhibitors for the Treatment of Parkinson's Disease", Progress in Medicinal Chemistry 56, 37-80 (2017).
Estrada, et al., "Chemical Biology of Leucine-Rich Repeat Kinase 2 (LRRK2) Inhibitors", Journal of Medicinal Chemistry 58, 6733-6746 (2015).
Estrada, et al., "Discovery of Highly Potent, Selective, and Brain-Penetrant Aminopyrazole Leucine-Rich Repeat Kinase 2 (LRRK2) Small Molecule Inhibitors", Journal of Medicinal Chemistry 57, 921-936 (2014).
Fuji, et al., "Effect of selective LRRK2 kinase inhibition on non-human primate lung", Science Translational Medicine 7 (273), 273ra15, 13 pages (2015).
Taymans, et al., "LRRK2 Kinase Inhibition as a Therapeutic Strategy for Parkinson's Disease, Where Do We Stand?", Current Neuropharmacology 14, 214-225 (2016).
Patent Cooperation Treaty, International Searching Authority, Search Report and Written Opinion for PCT US2018/062102, 8 pages, dated Feb. 8, 2019.
Pub Chem , "ZPPUMAMZIMPJGP-UHFFFAOYSA-N ", CID 69093374, 17 pages, Create Date Nov. 30, 2012.

PROCESS FOR THE PREPARATION OF PYRIMIDINYL-4-AMINOPYRAZOLE COMPOUNDS

CROSS REFERENCE TO RELATED APPLICATION

This application claims priority to U.S. Provisional Application No. 62/608,398 filed on 20 Dec. 2017, which is incorporated by reference herein.

FIELD

The present disclosure relates to methods of making pyrimidinyl-4-aminopyrazole compounds and intermediates thereof. The compounds are inhibitors of LRRK2 kinase and find use for treatment of LRRK2 mediated diseases such as Parkinson's disease.

BACKGROUND

Leucine-rich repeat kinase 2 (LRRK2) is a complex signaling protein that is a key therapeutic target, particularly in Parkinson's disease (PD). Combined genetic and biochemical evidence supports a hypothesis in which the LRRK2 kinase function is causally involved in the pathogenesis of sporadic and familial forms of PD, and therefore that LRRK2 kinase inhibitors could be useful for treatment (Christensen, K. V. (2017) Progress in medicinal chemistry 56:37-80). Inhibition of the kinase activity of LRRK2 is under investigation as a possible treatment for Parkinson's disease (Fuji, R. N. et al (2015) Science Translational Medicine 7(273):ra15; Taymans, J. M. et al (2016) Current Neuropharmacology 14(3):214-225). A group of LRRK2 kinase inhibitors have been studied (Estrada, A. A. et al (2015) Jour. Med. Chem. 58(17): 6733-6746; Estrada, A. A. et al (2013) Jour. Med. Chem. 57:921-936; Chen, H. et al (2012) Jour. Med. Chem. 55:5536-5545; Estrada, A. A. et al (2015) Jour. Med. Chem. 58:6733-6746; U.S. Pat. Nos. 8,354,420; 8,569,281; 8,791,130; 8,796,296; 8,802,674; 8,809,331; 8,815,882; 9,145,402; 9,212,173; 9,212,186; WO 2011/151360; WO 2012/062783; and WO 2013/079493.

DESCRIPTION

The present disclosure relates to methods of making pyrimidinyl-4-aminopyrazole compounds of formulae I and IV:

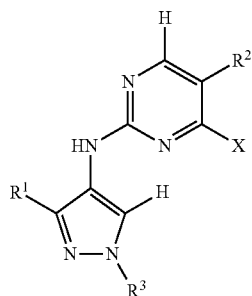

I

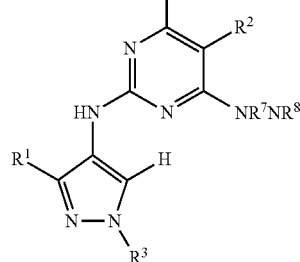

IV with the substituents X, $R^1$, $R^2$, $R^3$, $R^7$, $R^8$, and others described herein, along with reagents and intermediates used to prepare the compounds.

Definitions

The term "alkyl" as used herein refers to a saturated linear or branched-chain monovalent hydrocarbon radical of one to twelve carbon atoms ($C_1$-$C_{12}$), wherein the alkyl radical may be optionally substituted independently with one or more substituents described below. In another embodiment, an alkyl radical is one to eight carbon atoms ($C_1$-$C_8$), or one to six carbon atoms ($C_1$-$C_6$). Examples of alkyl groups include, but are not limited to, methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$), 1-heptyl, and 1-octyl.

The term "alkenyl" refers to linear or branched-chain monovalent hydrocarbon radical of two to twelve carbon atoms ($C_2$-$C_{12}$) with at least one site of unsaturation, i.e., a carbon-carbon, $sp^2$ double bond, wherein the alkenyl radical may be optionally substituted independently with one or more substituents described herein, and includes radicals having "cis" and "trans" orientations, or alternatively, "E" and "Z" orientations. Examples include, but are not limited to, ethylenyl or vinyl (—CH=$CH_2$), allyl (—$CH_2$CH=$CH_2$), and the like.

The term "alkynyl" refers to a linear or branched monovalent hydrocarbon radical of two to twelve carbon atoms ($C_2$-$C_{12}$) with at least one site of unsaturation, i.e., a carbon-carbon, sp triple bond, wherein the alkynyl radical may be optionally substituted independently with one or more substituents described herein. Examples include, but are not limited to, ethynyl (—C≡CH) and propynyl (propargyl, —$CH_2$C≡CH).

The terms "cycloalkyl", "carbocyclyl", "carbocyclic ring" and "carbocycle" refer to a monovalent non-aromatic, saturated or partially unsaturated ring having 3 to 10 carbon atoms ($C_3$-$C_{10}$) as a monocyclic ring or 7 to 12 carbon atoms as a bicyclic ring. Bicyclic cycloalkyls having 7 to 12 atoms can be arranged, for example, as a bicyclo [4,5], [5,5], [5,6] or [6,6] system, and bicyclic cycloalkyls having 9 or 10 ring atoms can be arranged as a bicyclo [5,6] or [6,6] system, or as bridged systems such as bicyclo[2.2.1]heptane, bicyclo [2.2.2]octane and bicyclo[3.2.2]nonane. Spiro cycloalkyl moieties are also included within the scope of this definition. Examples of spiro cycloalkyl moieties include [2.2]pentanyl, [2.3]hexanyl, and [2.4]heptanyl. Examples of monocyclic cycloalkyls include, but are not limited to, cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl and cyclododecyl. Cycloalkyl groups are optionally substituted independently with one or more substituents described herein.

The terms "heterocycle," "heterocyclyl" and "heterocyclic ring" are used interchangeably herein and refer to a saturated or a partially unsaturated (i.e., having one or more double and/or triple bonds within the ring) carbocyclic radical of 3 to about 20 ring atoms in which at least one ring atom is a heteroatom selected from nitrogen, oxygen, phosphorus and sulfur, the remaining ring atoms being C, where one or more ring atoms is optionally substituted independently with one or more substituents described below. A heterocycle may be a monocycle having 3 to 7 ring members (2 to 6 carbon atoms and 1 to 4 heteroatoms selected from N, O, P, and S) or a bicycle having 7 to 10 ring members (4 to 9 carbon atoms and 1 to 6 heteroatoms selected from N, O, P, and S), for example: a bicyclo [4,5], [5,5], [5,6], or [6,6] system. Heterocycles are described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and J. Am. Chem. Soc. (1960) 82:5566. "Heterocyclyl" also includes radicals where heterocycle radicals are fused with a saturated, partially unsaturated ring, or aromatic carbocyclic or heterocyclic ring. Examples of heterocyclic rings include, but are not limited to, morpholin-4-yl, piperidin-1-yl, piperazinyl, piperazin-4-yl-2-one, piperazin-4-yl-3-one, pyrrolidin-1-yl, thiomorpholin-4-yl, S-dioxothiomorpholin-4-yl, azocan-1-yl, azetidin-1-yl, octahydropyrido[1,2-a]pyrazin-2-yl, [1,4] diazepan-1-yl, pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, homopiperazinyl, azetidinyl, oxetanyl, thietanyl, homopiperidinyl, oxepanyl, thiepanyl, oxazepinyl, diazepinyl, thiazepinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinylimidazolinyl, imidazolidinyl, 3-azabicyco[3.1.0]hexanyl, 3-azabicyclo[4.1.0]heptanyl, azabicyclo[2.2.2]hexanyl, 3H-indolyl quinolizinyl and N-pyridyl ureas. Spiro heterocyclyl moieties are also included within the scope of this definition. Examples of spiro heterocyclyl moieties include azaspiro[2.5]octanyl and azaspiro[2.4]heptanyl. Examples of a heterocyclic group wherein 2 ring atoms are substituted with oxo (═O) moieties are pyrimidinonyl and 1,1-dioxo-thiomorpholinyl. The heterocycle groups herein are optionally substituted independently with one or more substituents described herein.

"Aryl" means a monovalent aromatic hydrocarbon radical of 6-20 carbon atoms ($C_6$-$C_{20}$) derived by the removal of one hydrogen atom from a single carbon atom of a parent aromatic ring system. Some aryl groups are represented in the exemplary structures as "Ar". Aryl includes bicyclic radicals comprising an aromatic ring fused to a saturated, partially unsaturated ring, or aromatic carbocyclic ring. Typical aryl groups include, but are not limited to, radicals derived from benzene (phenyl), substituted benzenes, naphthalene, anthracene, biphenyl, indenyl, indanyl, 1,2-dihydronaphthalene and 1,2,3,4-tetrahydronaphthyl. Aryl groups are optionally substituted independently with one or more substituents described herein.

The term "heteroaryl" refers to a monovalent aromatic radical of 5-, 6-, or 7-membered rings, and includes fused ring systems (at least one of which is aromatic) of 5-20 atoms, containing one or more heteroatoms independently selected from nitrogen, oxygen, and sulfur. Examples of heteroaryl groups are pyridinyl (including, for example, 2-hydroxypyridinyl), imidazolyl, imidazopyridinyl, pyrimidinyl (including, for example, 4-hydroxypyrimidinyl), pyrazolyl, triazolyl, pyrazinyl, tetrazolyl, furyl, thienyl, isoxazolyl, thiazolyl, oxadiazolyl, oxazolyl, isothiazolyl, pyrrolyl, quinolinyl, isoquinolinyl, tetrahydroisoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. Heteroaryl groups are optionally substituted independently with one or more substituents described herein.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., "Stereochemistry of Organic Compounds", John Wiley & Sons, Inc., New York, 1994. The compounds of the present disclosure may contain asymmetric or chiral centers (stereocenters), and therefore exist in different stereoisomeric forms. It is intended that all stereoisomeric forms of the compounds of the present disclosure, including but not limited to, diastereomers, enantiomers and atropisomers, as well as mixtures thereof such as racemic mixtures, form part of the present disclosure. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

The term "leaving group" refers to electron withdrawing groups that can be displaced upon reaction with a nucleophile. Examples of leaving groups include halo, nitro ($NO_2$), sulfones, and sulfates (e.g. triflates or sulfone or sulfate substituted with alkyl, aryl, or heteroaryl, wherein each alkyl, aryl, or heteroaryl is optionally substituted with one or more groups selected from halo, hydroxy, amino, nitro, cyano, and ($C_1$-$C_6$) alkoxy). Examples of leaving groups also include aryloxy (—OAr) such as phenoxy, and alkoxy (—O-alkyl) such as —O—($C_1$-$C_6$) alkyl where each aryl and alkyl is optionally substituted with one or more groups selected from halo, hydroxy, amino, nitro, cyano, and ($C_1$-$C_6$) alkoxy).

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

Preparation of Pyrimidinyl-4-Aminopyrazole Compounds

The present disclosure includes processes, methods, reagents, and intermediates for the synthesis of pyrimidinyl-4-aminopyrazole compounds of formulae I and IV:

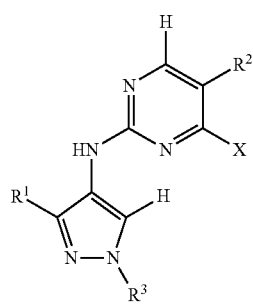

I

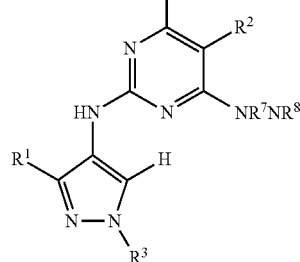

IV

In some embodiments the compounds of formula I are prepared from compounds of formula II and III and result in the regioselective formation of formula I. In such embodiments the coupling between formulas II and III favors displacement of the L group over that of the X group of formula III.

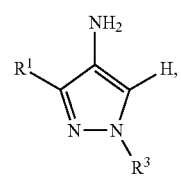

II

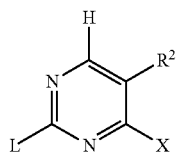

III

An aspect of the present disclosure is a process for the preparation of a compound of formula I:

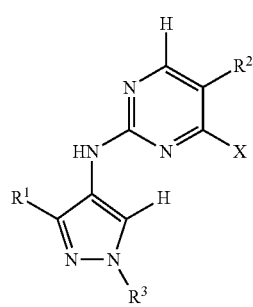

I or a salt thereof, wherein:

X is selected from halo, $NO_2$, $SO_2R^6$, $SO_3R^6$, —OAr and O—($C_1$-$C_6$) alkyl;

$R^1$ is selected from halo, cyano, $C_{1-12}$ alkyl, $C_{2-12}$ alkenyl, $C_{2-12}$ alkynyl, $C_{1-12}$ alkoxy, $C_{3-10}$ cycloalkyl, heterocyclyl, aryl and heteroaryl, wherein each alkyl, alkenyl, alkynyl, alkoxy, cycloalkyl, heterocyclyl, aryl and heteroaryl of $R^1$ is optionally and independently substituted with one or more groups selected from halo, hydroxy, amino, nitro, cyano, ($C_1$-$C_6$) alkoxy, and oxo (=O);

$R^2$ is selected from halo, cyano, $C_{1-12}$ alkyl, —C(O)$R^4$, —C(O)O$R^4$ and —C(O)N($R^4$)($R^5$), wherein the alkyl of $R^2$ is optionally substituted with one or more halo or $C_{1-3}$ alkoxy;

$R^3$ is selected from hydrogen, —CN, $C_{1-12}$ alkyl, $C_{2-12}$ alkenyl, $C_{2-12}$ alkynyl, —C(O)$R^4$, —C(O)O$R^4$, —C(O)N$R^4R^5$, —($C_{1-12}$ alkyl)C(O)N$R^4R^5$, —S(O)$_{0-2}R^4$, —S(O)$_{0-2}$N$R^4R^5$, —($C_{1-12}$ alkyl)S(O)$_{0-2}$N$R^4R^5$, —($C_{1-12}$ alkyl)CN, ($C_{1-12}$ alkyl)-C(O)$R^4$, —($C_{1-12}$ alkyl)-C(O)O$R^4$, $C_{3-10}$ cycloalkyl, heterocyclyl, aryl and heteroaryl, wherein each alkyl, alkenyl, alkynyl, cycloalkyl, heterocyclyl, aryl and heteroaryl of $R^3$ is independently and optionally substituted with one or more groups selected from halo, hydroxy, amino, nitro, cyano, ($C_1$-$C_6$) alkoxy, and oxo (=O); and each $R^4$ and $R^5$ is independently selected from hydrogen, $C_{1-12}$ alkyl, $C_{2-12}$ alkenyl, $C_{2-12}$ alkynyl, $C_{1-12}$ alkoxy, $C_{3-10}$ cycloalkyl, heterocyclyl, aryl and heteroaryl, wherein each alkyl, alkenyl, alkynyl, alkoxy, cycloalkyl, heterocyclyl, aryl and heteroaryl of $R^4$ or $R^5$ are independently and optionally substituted with one or more groups selected from halo, hydroxy, amino, nitro, cyano, ($C_1$-$C_6$) alkoxy, and oxo (=O); or $R^4$ and $R^5$ are taken together with the atoms to which they are attached to form an optionally substituted heterocyclyl; and $R^6$ is selected from $C_{1-12}$ alkyl, aryl, and heteroaryl, each optionally substituted with one or more groups selected from halo, hydroxy, amino, nitro, cyano, and ($C_1$-$C_6$) alkoxy;

the process comprising:

contacting a compound of formula II:

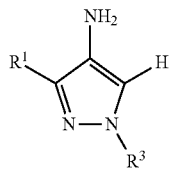

II or a salt thereof, with a compound of formula III:

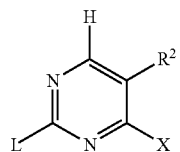

III or a salt thereof, wherein L is a leaving group;

under conditions sufficient to form a compound of formula I or a salt thereof; and optionally (b) purifying the compound of formula I or salt thereof.

In an exemplary embodiment, X is halo and L is halo.

In an exemplary embodiment, X is chloro and L is chloro.

In an exemplary embodiment, X is —OAr and L is halo.

In an exemplary embodiment, X is —OAr or —O—($C_1$-$C_6$) alkyl, and L is —OAr or —O—($C_1$-$C_6$) alkyl.

In an exemplary embodiment, $R^1$ is optionally substituted $C_{1-12}$ alkyl.

In an exemplary embodiment, $R^1$ is $CH_3$.

In an exemplary embodiment, $R^2$ is optionally substituted methyl.

In an exemplary embodiment, $R^2$ is $CF_3$.

In an exemplary embodiment, $R^3$ of formula I is ($C_{1-12}$ alkyl)-C(O)N$R^4R^5$.

In an exemplary embodiment, $R^3$ of formula I is —C(CH$_3$)$_2$C(O)NH$_2$.

The process may further comprise contacting a compound of formula II and a compound of formula III with a Lewis acid selected from ZnCl$_2$, CuI/BF$_3$ etherate, trimethylsilyl trifluoromethanesulfonate (TMSOTf), TiCl$_4$, BiCl$_3$, InCl$_3$, BCl$_3$, Et$_2$Zn, and ZnBr$_2$.

An exemplary embodiment, the Lewis acid is zinc chloride.

An exemplary embodiment, the formula II compound and zinc chloride are mixed in a solvent and the mixture is added to the formula III compound.

The process may further comprise contacting a compound of formula I with a compound of the formula NHR$^7$R$^8$ or a salt thereof to form a compound of formula IV:

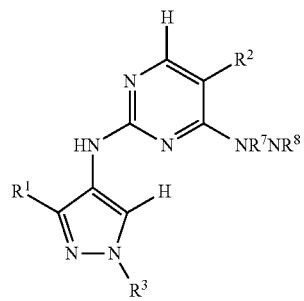

IV or a salt thereof; wherein $R^1$, $R^2$, and $R^3$ are as previously defined for Formula I;

each $R^7$ and $R^8$ is independently selected from hydrogen, $C_{1-12}$ alkyl, $C_{2-12}$ alkenyl, $C_{2-12}$ alkynyl, $C_{3-10}$ cycloalkyl, heterocyclyl, aryl and heteroaryl, wherein each alkyl, alkenyl, alkynyl, cycloalkyl, heterocyclyl, aryl and heteroaryl of $R^7$ or $R^8$ are independently and optionally substituted with one or more groups selected from halo, hydroxy, amino, nitro, cyano, ($C_1$-$C_6$) alkoxy, and oxo (=O); or $R^7$ and $R^8$ are taken together with the atoms to which they are attached to form an optionally substituted heterocyclyl.

In an exemplary embodiment, $R^7$ and $R^8$ are independently hydrogen or $C_{1-12}$ alkyl optionally substituted with oxo, halo, amino or hydroxyl.

In an exemplary embodiment, $R^7$ is methyl or ethyl, and $R^8$ is hydrogen.

In an exemplary embodiment, $R^3$ of formula I is —($C_{1-12}$ alkyl)-NR$^4$R$^5$.

In an exemplary embodiment, $R^3$ of formula I is —C(CH$_3$)$_2$C(O)NH$_2$.

The process may further comprise contacting a compound of formula IV, with a dehydrating agent to form a compound of formula IV, wherein $R^3$ is —C(CH$_3$)$_2$CN, or a salt thereof.

In an exemplary embodiment, the dehydrating agent is phosphoryl trichloride (POCl$_3$), propane phosphonic acid anhydride (T3P), phosphorous pentoxide (P$_2$O$_5$), or trifluoroacetic anhydride ((CF$_3$CO)$_2$O).

The process may further comprise purifying the compound or salt thereof formed.

The process may further comprise contacting the compound with an excipient and processing the resulting composition into a capsule or tablet.

In an exemplary embodiment, X is halo; $R^1$ is methyl, $R^2$ is trifluoromethyl, $R^3$ is —$C(CH_3)_2C(O)NH_2$, and L is halo.

In an exemplary embodiment, X and L are chloro.

In another aspect provided is a compound of formula V:

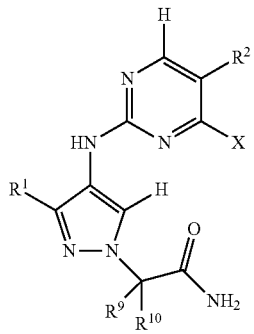

or a salt, stereoisomer, tautomer or deuterium analog thereof, wherein:

X is selected from halo, $NO_2$, $SO_2R^6$, $SO_3R^6$, —OAr and —O—($C_1$-$C_6$) alkyl;

$R^1$ is selected from halo, cyano, $C_{1-12}$ alkyl, $C_{2-12}$ alkenyl, $C_{2-12}$ alkynyl, $C_{1-12}$ alkoxy, $C_{3-10}$ cycloalkyl, heterocyclyl, aryl and heteroaryl, wherein each alkyl, alkenyl, alkynyl, alkoxy, cycloalkyl, heterocyclyl, aryl and heteroaryl of $R^1$ is optionally and independently substituted with one or more groups selected from halo, hydroxy, amino, nitro, cyano, ($C_1$-$C_6$) alkoxy, and oxo (=O);

$R^2$ is selected from halo, cyano, $C_{1-12}$ alkyl, —$C(O)R^4$, —$C(O)OR^4$ and —$C(O)N(R^4)(R^5)$, wherein the alkyl of $R^2$ is optionally substituted with one or more halo or $C_{1-3}$ alkoxy;

each $R^4$ and $R^5$ is independently selected from hydrogen, $C_{1-12}$ alkyl, $C_{2-12}$ alkenyl, $C_{2-12}$ alkynyl, $C_{1-12}$ alkoxy, $C_{3-10}$ cycloalkyl, heterocyclyl, aryl and heteroaryl, wherein each alkyl, alkenyl, alkynyl, alkoxy, cycloalkyl, heterocyclyl, aryl and heteroaryl of $R^4$ or $R^5$ are independently and optionally substituted with one or more groups selected from halo, hydroxy, amino, nitro, cyano, ($C_1$-$C_6$) alkoxy, and oxo (=O); or $R^4$ and $R^5$ are taken together with the atoms to which they are attached to form an optionally substituted heterocyclyl;

$R^6$ is selected from $C_{1-12}$ alkyl, aryl, and heteroaryl, each optionally substituted with one or more groups selected from halo, hydroxy, amino, nitro, cyano, and ($C_1$-$C_6$) alkoxy; and $R^9$ and $R^{10}$ are independently hydrogen or $C_{1-12}$ alkyl optionally substituted with one or more groups selected from halo, hydroxy, amino, nitro, cyano, ($C_1$-$C_6$) alkoxy, and oxo (=O).

In an exemplary embodiment, X is halo.

In an exemplary embodiment, X is chloro.

In an exemplary embodiment, X is chloro; $R^1$ is $C_{1-12}$ alkyl; $R^2$ is $C_{1-12}$ alkyl substituted with one or more F; and $R^9$ and $R^{10}$ are independently optionally substituted alkyl.

In an exemplary embodiment, $R^9$ and $R^{10}$ are alkyl.

In an exemplary embodiment, X is chloro; $R^1$ is $CH_3$, $R^2$ is $CF_3$; and $R^9$ and $R^{10}$ are $CH_3$.

In an exemplary embodiment, X is OAr or O—($C_1$-$C_6$) alkyl.

The compounds of Formula V are useful as an intermediate in the synthesis of LRRK2 inhibitors.

The compounds of the present disclosure may contain asymmetric or chiral centers, and therefore exist in different stereoisomeric forms. It is intended that all stereoisomeric forms of the compounds of the present disclosure, including but not limited to, diastereomers, enantiomers and atropisomers, as well as mixtures thereof such as racemic, diastereomeric, or enantiomerically-enriched mixtures, form part of the present disclosure. In addition, the present disclosure embraces all geometric and positional isomers. In the structures shown herein, where the stereochemistry of any particular chiral atom is not specified, then all stereoisomers are contemplated and included as the compounds of the present disclosure. Where stereochemistry is specified by a solid wedge or dashed line representing a particular configuration, then that stereoisomer is so specified and defined.

The compounds of the present disclosure may exist in unsolvated as well as solvated forms with pharmaceutically acceptable solvents such as water, ethanol, and the like, and it is intended that the present disclosure embraces both solvated and unsolvated forms.

The compounds of the present disclosure may also exist in different tautomeric forms, and all such forms are embraced within the scope of the present disclosure. The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

The compounds of the present disclosure also include isotopically-labeled compounds which are identical to those recited herein, but for the fact that one or more atoms are replaced by an atom having an atomic mass or mass number different from the atomic mass or mass number usually found in nature. All isotopes of any particular atom or element as specified are contemplated within the scope of the compounds of the present disclosure, and their uses. Exemplary isotopes that can be incorporated into compounds of the present disclosure include isotopes of hydrogen, carbon, nitrogen, oxygen, phosphorus, sulfur, fluorine, chlorine and iodine, such as $^2H$, $^3H$, $^{11}C$, $^{13}C$, $^{14}C$, $^{13}N$, $^{15}N$, $^{15}O$, $^{17}O$, $^{18}O$, $^{32}P$, $^{33}P$, $^{35}S$, $^{18}F$, $^{36}Cl$, $^{123}I$ and $^{125}I$. Certain isotopically-labeled compounds of the present disclosure (e.g., those labeled with $^3H$ and $^{14}C$) are useful in compound and/or substrate tissue distribution assays. Tritiated ($^3H$) and carbon-14 ($^{14}C$) isotopes are useful for their ease of preparation and detectability. Further, substitution with heavier isotopes such as deuterium (i.e., $^2H$) may afford certain therapeutic advantages resulting from greater metabolic stability (e.g., increased in vivo half-life or reduced dosage requirements) and hence may be preferred in some circumstances. Positron emitting isotopes such as $^{15}O$, $^{13}N$, $^{11}C$ and $^{18}F$ are useful for positron emission tomography (PET) studies to examine substrate receptor occupancy. Isotopically labeled compounds of the present disclosure can generally be prepared by following procedures analogous to those disclosed in the Examples herein below, by substituting an isotopically labeled reagent for a non-isotopically labeled reagent.

Compounds having LRKK2 activity can be readily determined according to known assays, such as those disclosed in WO 2011/151360, WO 2012/062783, and WO 2013/079493.

Starting materials and reagents for the preparation of compounds of the present disclosure are generally available from commercial sources or are readily prepared using methods well known to those skilled in the art (e.g., prepared by methods generally described in Louis F. Fieser and Mary Fieser, *Reagents for Organic Synthesis*, v. 1-19, Wiley, N.Y. (1967-1999 ed.), or *Beilsteins Handbuch der organischen Chemie*, 4, Aufl. ed. Springer-Verlag, Berlin, including supplements (also available via the Beilstein online database).

The following Schemes 1-4 illustrate the chemical reactions, processes, methodology for the synthesis of compounds of the present disclosure, as well as certain intermediates and reagents.

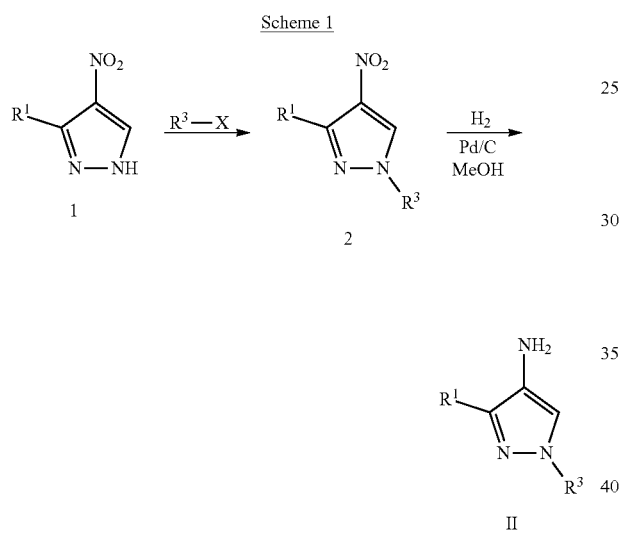

Scheme 1 shows the N-1 substitution and nitro reduction of a 3-substituted-4-nitro-1H-pyrazole compound 1. Alkylation or acylation of 1 gives N-1 substituted product 2 along with some N-2 substituted regioisomer depending on the $R^1$ group and alkylating/acylating reagent $R^3$—X. Hydrogenation of the nitro group of 2 can be conducted with hydrogen gas and a catalyst such as palladium on carbon in a protic solvent to give 1, 3-disubstituted-4-amino-1H-pyrazole compound II.

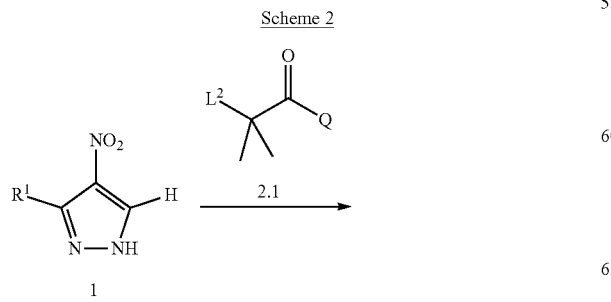

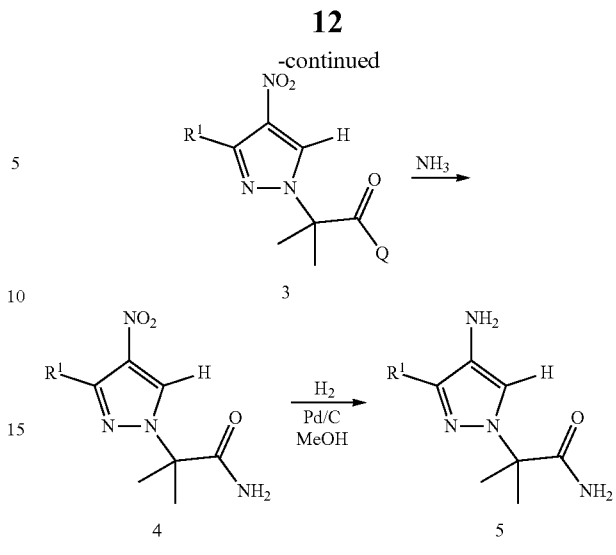

Scheme 2 shows N-1 alkylation of a 3-substituted-4-nitro-1H-pyrazole compound 1 with an alkylating agent 2.1, wherein $L^2$ is halo or OH, and Q is OH, $NH_2$, $NH(C_{1-6}$ alkyl), $NH(C_{1-6}$ alkyl)($C_{1-6}$ alkyl), or $C_{1-6}$ alkoxy, wherein the $C_{1-6}$ alkyl and $C_{1-6}$ alkoxy are optionally substituted with one or more halo. In one embodiment compound 2.1 is methyl 2-bromo-2-methylpropanoate ($L^2$=Br, Q=OCH$_3$), and is reacted with compound 1 in the presence of a base such as cesium carbonate or potassium carbonate to give N-1 substituted product 3 along with some N-2 substituted regioisomer depending on the $R^1$ group. Ammonolysis of the methyl ester of 3 gives amide 4. Ammonolysis can be carried out using ammonia such as gaseous $NH_3$ or in a protic solvent such as methanol or water or an aprotic solvent. Hydrogenation of the nitro group of 4 can be conducted with hydrogen gas and a catalyst such as palladium on carbon in a protic solvent to give 1, 3-disubstituted-4-amino-1H-pyrazole compound 5.

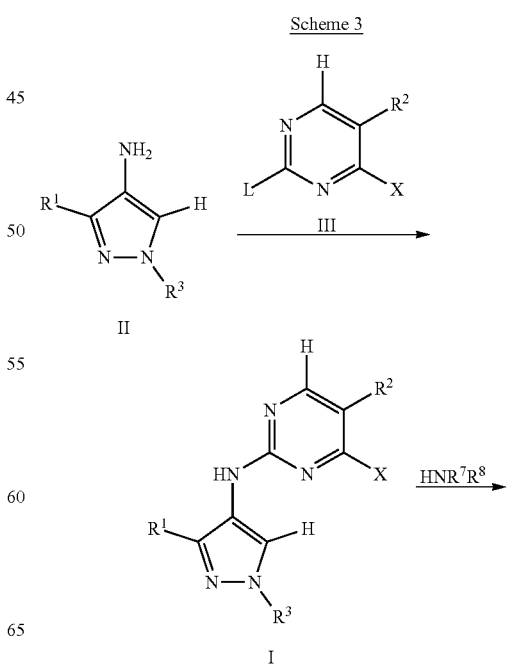

-continued

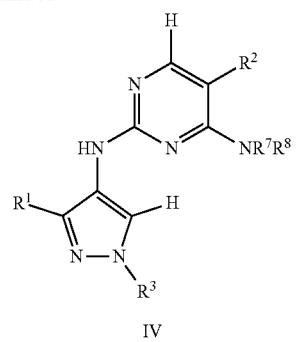

IV

Scheme 3 shows coupling of 4-amino pyrazole intermediates II with 2,4-disubstituted pyrimidine intermediates III to give I. Although not limited by any particular mechanism, this reaction may proceed by a regioselective SNAr nucleophilic aromatic substitution mechanism (March's Advanced Organic Chemistry, 6th Ed. (2007), John Wiley & Sons). Displacement of X (halo) from I with an amine HNR[7]R[8] gives IV.

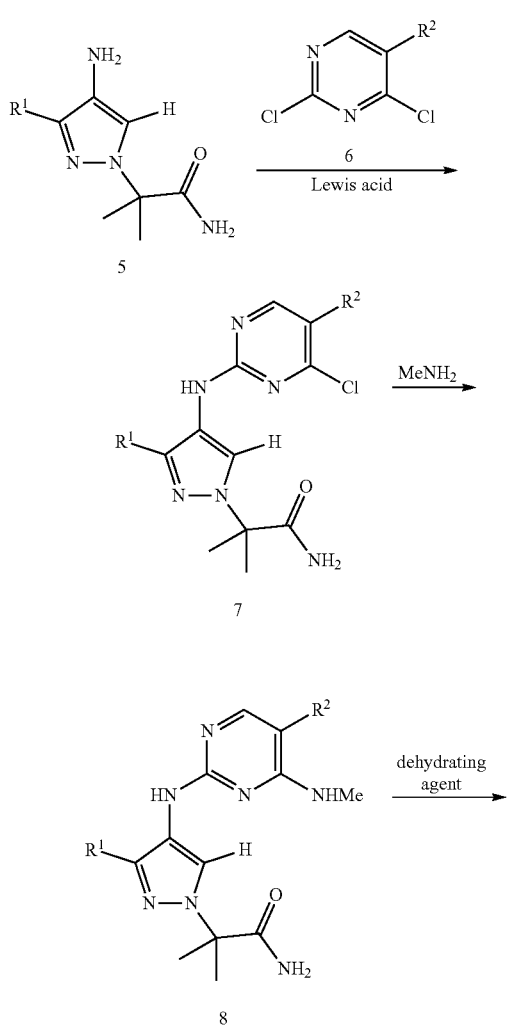

-continued

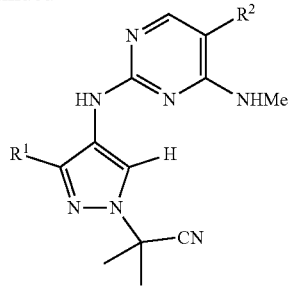

9

Scheme 4 shows a more specific example of the process of Scheme 3. Coupling of the 2-(4-amino-3-substituted-1H-pyrazol-1-yl)-2-methylpropanamide 5 with the 2,4-dichloro-5-substituted pyrimidine 6 and a Lewis Acid such as zinc chloride gives the 2-(4-((4-chloro-5-substituted pyrimidin-2-yl)amino)-3-substituted-1H-pyrazol-1-yl)-2-methylpropanamide intermediate 7 in a regioselective SNAr reaction. Displacement of chloride with methylammonium chloride or methylamine freebase, gives the 2-(4-((5-substituted-4-(methyl amino)pyrimidin-2-yl)amino)-3-substituted-1H-pyrazol-1-yl)-2-methylpropanamide 8. Such displacement can be carried out using excess methylamine or in the presence of an organic or inorganic base. In some embodiments the displacement is carried out with excess methyl amine free base in tetrahydrofuran. In other embodiments the displacement is carried out with methyl amine hydrochloride in N-methyl-2-pyrrolidone (NMP) with an organic amine base such as N,N-diisopropylethylamine. Dehydration of the amide of 8 with a dehydrating agent such as phosphoryl trichloride (POCl$_3$) or propane phosphonic acid anhydride (T3P) forms the nitrile compound 9. Alternatively, dehydration can be conducted with methanesulfonic anhydride and a base such as pyridine (Org. Process Res. Dev. 2016, 20, 140-177), or alternative methods as described in Larock, R. C. & Yao, T. "Interconversion of nitrites, carboxylic adds and derivatives" in a Guide to Functional Group Preparations, Comprehensive organic Transformations, Wiley-VCH Publishers, (2018).

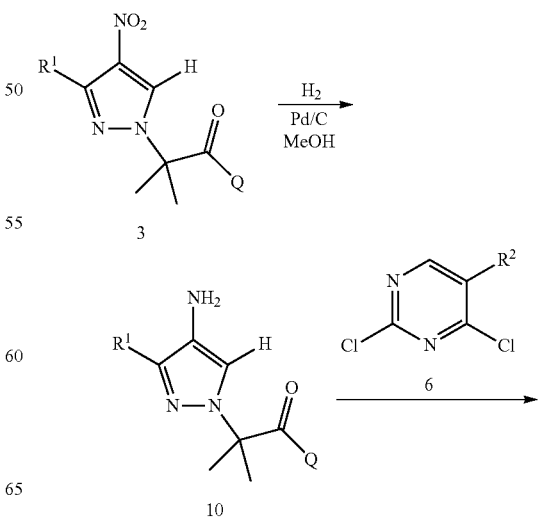

-continued

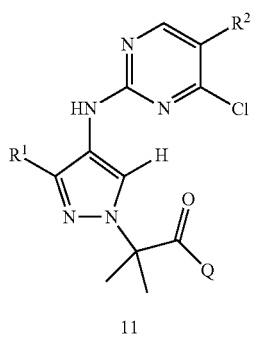

11

Scheme 5 shows another specific example of the process of Scheme 3. Reduction of the nitro group of 3 where Q is $C_{1-6}$ alkoxy by catalytic hydrogenation forms 10. Coupling of 10 with the 2,4-dichloro-5-substituted pyrimidine 6 gives ester 11 in a regioselective SNAr reaction. The coupling can be conducted in the presence of a Lewis Acid such as zinc chloride. Intermediate 11 can be further elaborated according to the Schemes and Examples to form formula IV and V compounds.

EXAMPLES

Compounds were characterized and structures confirmed by NMR. The samples for NMR analysis were prepared by complete dissolution of an appropriate amount of material in deuterated solvent (DMSO-$d_6$, $CD_3CN$, or $CDCl_3$). $^1H$ NMR spectra were recorded at 25° C. using either a Varian INOVA 400 MHz NMR Spectrometer equipped with a Varian ATB probe or a Varian INOVA 600 MHz NMR Spectrometer equipped with a Varian 5 mm $^1H$ {C13/N15} triple resonance cold probe.

Example 1 Preparation of 2-(4-amino-3-methyl-1H-pyrazol-1-yl)-2-methylpropanamide 5a

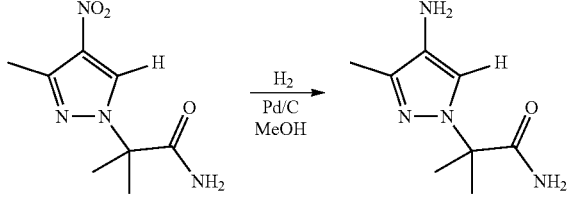

To a 20-L reactor containing dimethyl formamide (4.5 L) was charged 5-methyl-4-nitro-1H-pyrazole 1a (1.5 kg, 1.0 equiv). The solution was cooled to 0° C. and charged with finely ground $K_2CO_3$ (2.45 kg, 1.5 equiv) in three portions over 1 h. Methyl 2-bromo-2-methylpropanoate (3.2 kg, 1.5 equiv) was added dropwise to the mixture and then was allowed to warm to 25° C. The reaction mixture was maintained for 16 h and then quenched with water (15 L) and product was extracted with ethyl acetate. The combined organic layer was washed with water, and then with a brine. The organic layer was dried over anhydrous $Na_2SO_4$, filtered, and concentrated under reduced pressure to give a light yellow solid. The crude product was purified by crystallization with petroleum ether (15 L), filtered, and dried to give methyl 2-methyl-2-(3-methyl-4-nitro-1H-pyrazol-1-yl)propanoate 3a (2.25 kg, >99% purity by HPLC, 84% yield) as an off-white solid. $^1H$ NMR (400 MHz, $CDCl_3$) 8.28 (s, 1H), 3.74 (s, 3H), 2.53 (s, 3H), 1.85 (s, 6H).

Methanol (23 L) and 2-methyl-2-(3-methyl-4-nitro-1H-pyrazol-1-yl)propanoate 3a (2.25 kg, 1.0 equiv) were charged into a 50-L reactor and cooled to approximately −20° C. Ammonia gas was purged over a period of 5 h and then the reaction mixture warmed to 25° C. After 16 h, the reaction mixture was concentrated under reduced pressure (~50° C.) to give the crude product. Ethyl acetate (23 L) was charged and the solution agitated in the presence of charcoal (0.1 w/w) and Celite® (0.1 w/w) at 45° C. The mixture was filtered and concentrated under reduced pressure, and then the solid was slurried in methyl tert-butyl ether (MTBE, 11.3 L) at RT for 2 h. Filtration and drying at ~45° C. gave 2-methyl-2-(3-methyl-4-nitro-1H-pyrazol-1-yl)propanamide 4a (1.94 kg, >99% purity by HPLC, 92% yield).

Methanol (5 L) and 2-methyl-2-(3-methyl-4-nitro-1H-pyrazol-1-yl)propanamide 4a (0.5 kg) were charged into a 10-L autoclave under nitrogen atmosphere, followed by slow addition of 10% (50% wet) Pd/C (50 g). Hydrogen was charged (8.0 kg pressure/113 psi) and the reaction mixture agitated at 25° C. until complete. The mixture was filtered, concentrated under reduced pressure and then slurried in MTBE (2.5 L) for 2 h at 25° C. Filtration and drying under reduced pressure (45° C.) gave 2-(4-amino-3-methyl-1H-pyrazol-1-yl)-2-methylpropanamide 5a (0.43 kg, >99% purity by HPLC, 99% yield).

Example 2 Preparation of 2-(4-((4-chloro-5-(trifluoromethyl)pyrimidin-2-yl)amino)-3-methyl-1H-pyrazol-1-yl)-2-methylpropanamide 7a

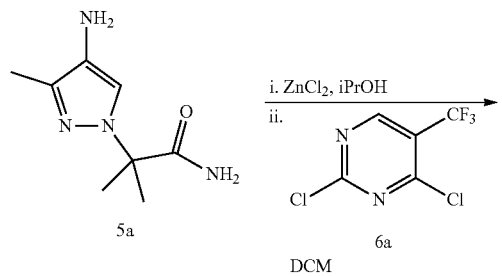 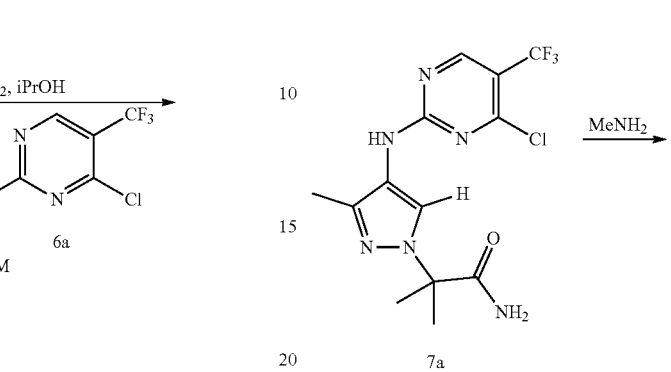

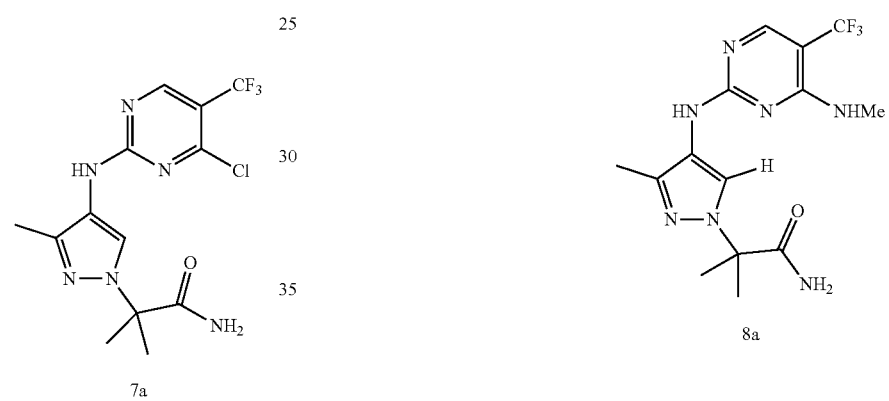

Into a first reactor was charged t-BuOH (or alternatively 2-propanol) (15.5 vol) and 2-(4-amino-3-methyl-1H-pyrazol-1-yl)-2-methylpropanamide 5a (15 kg), followed by zinc chloride (13.5 kg, 1.2 equiv) at room temperature and the suspension agitated ~2 h. Into a second reactor was charged dichloromethane (DCM, 26.6 vol) and 2,4-dichloro-5-trifluoromethyl pyrimidine 6a (19.6 kg, 1.1 equiv) and then cooled to 0° C. The contents from first reactor were added portion-wise to the second reactor. After addition, the reaction mixture was agitated at 0° C. for ~1 h and then Et₃N (9.2 kg, 1.1 equiv) was slowly charged. After agitation for 1 h, the temperature was increased to 25° C. and monitored for consumption of starting material. The reaction mixture was quenched with 5% aqueous NaHCO₃ and then filtered over Celite®. The DCM layer was removed and the aqueous layer was back-extracted with DCM (3×). The combined organics were washed with water, dried (Na₂SO₄), and concentrated. Methanol (2.5 vol) was charged and the solution was heated to reflux for 1 h, then cooled to 0° C. After 1 h, the solids were filtered and dried under reduced pressure to give 2-(4-((4-chloro-5-(trifluoromethyl)pyrimidin-2-yl)amino)-3-methyl-1H-pyrazol-1-yl)-2-methylpropanamide 7a (31.2 kg (wet weight)). ¹H NMR (600 MHz, DMSO-d₆) 10.05 (br. s., 1H), 8.71 (d, J=11 Hz, 1H), 7.95 (app. d, 1H), 7.18 (br. s., 1H), 6.78 (br. s., 1H), 2.14 (s, 3H), 1.67 (s, 6H).

Example 3 Preparation of 2-methyl-2-(3-methyl-4-((4-(methylamino)-5-(trifluoromethyl)pyrimidin-2-yl)amino)-1H-pyrazol-1-yl)propanamide 8a A reactor was charged with anhydrous tetrahydrofuran (THF, 10 vol) and 2-(4-((4-chloro-5-(trifluoromethyl)pyrimidin-2-yl)amino)-3-methyl-1H-pyrazol-1-yl)-2-methylpropanamide 7a (21 kg) at room temperature with agitation. A solution of 2M methylamine in THF (3.6 vol) was slowly charged to the reactor at 25° C. and maintained for ~3 h. The reaction mixture was diluted with 0.5 w/w aqueous sodium bicarbonate solution (10 w/w), and extracted with ethyl acetate (EtOAc, 4.5 w/w). The aqueous layer was extracted with EtOAc (4×), the organics were combined and then washed with H₂O (7 w/w). The organic layer was dried over sodium sulfate, filtered and concentrated under reduced pressure. n-Heptane (3 w/v) was added to the residue, agitated, filtered and dried under reduced pressure to give 2-methyl-2-(3-methyl-4-((4-(methylamino)-5-(trifluoromethyl)pyrimidin-2-yl)amino)-1H-pyrazol-1-yl)propanamide 8a (19.15 kg, 93% yield). ¹H NMR (600 MHz, DMSO-d₆) 8.85 (m, 1H), 8.10 (s, 1H), 8.00 (m, 1H), 7.16 (br. s., 1H), 6.94 (m, 1H), 6.61 (br. s., 1H), 2.90 (d, J=4.3 Hz, 3H), 2.18 (br. s., 3H), 1.65 (s, 6H).

Example 4 Preparation of 2-methyl-2-(3-methyl-4-((4-(methylamino)-5-(trifluoromethyl)pyrimidin-2-yl)amino)-1H-pyrazol-1-yl)propanenitrile 9a

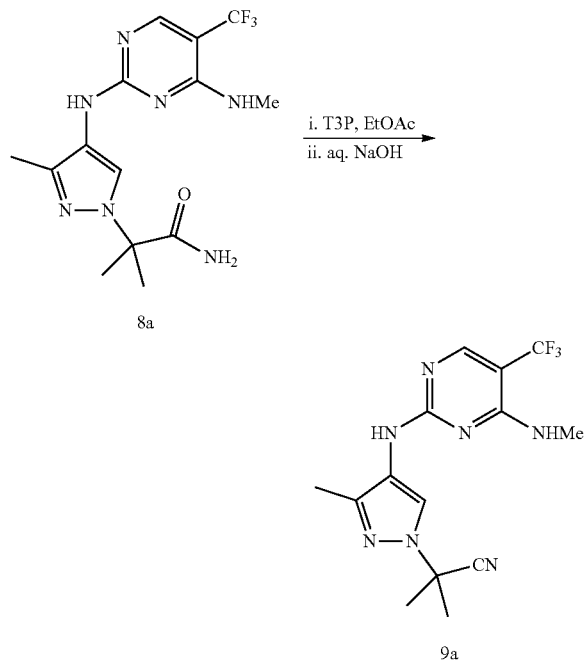

To a reactor was charged 2-methyl-2-(3-methyl-4-((4-(methylamino)-5-(trifluoromethyl)pyrimidin-2-yl)amino)-1H-pyrazol-1-yl)propanamide 8a (15 kg, 1 equiv) at room temperature followed by EtOAc (2 vol) and 6.7 vol T3P (50% w/w in EtOAc). The reaction mixture was heated to 75° C. over 1 h and then agitated for 16 h until consumption of starting material. The reaction mixture was cooled between −10 to −15° C. then added drop-wise 5N aqueous NaOH (7 vol) resulting in pH 8-9. The layers were separated and the aqueous layer back-extracted with EtOAc (2×4 vol). The combined organic extracts were washed with 5% aqueous NaHCO$_3$ solution, and then distilled to azeotropically remove water. The organics were further concentrated, charged with n-heptane (2 vol) and agitated for 1 h at room temperature. The solids were filtered, rinsed with n-heptane (0.5 vol) and then dried under vacuum (<50° C.). The dried solids were dissolved in EtOAc (1.5 vol) at 55° C., and then n-heptane (3 vol) was slowly added followed by 5-10% of 9a seeds. To the mixture was slowly added n-heptane (7 vol) at 55° C., agitated for 1 h, cooled to room temperature and then maintained for 16 h. The suspension was further cooled between 0-5° C., agitated for 1 hour, filtered, and then rinsed the filter with chilled 1:6.5 EtOAc/n-heptane (1 vol). The product was dried under vacuum at 50° C. to give 2-methyl-2-(3-methyl-44(4-(methylamino)-5-(trifluoromethyl)pyrimidin-2-yl)amino)-1H-pyrazol-1-yl)propanenitrile 9a (9.5 kg, first crop), 67% yield). $^1$H NMR (600 MHz, DMSO-d$_6$) 8.14 (s, 1H), 8.13 (br. s., 1H), 7.12 (br. s., 1H), 5.72 (br. s, 1H), 3.00 (d, J=4.6 Hz, 3H), 2.23 (s, 3H), 1.96 (s, 3H).

Example 5 Preparation of methyl 2-(4-amino-3-methyl-1H-pyrazol-1-yl)-2-methylpropanoate 10a

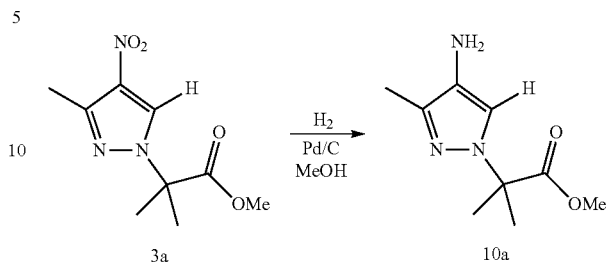

Following the procedure of Example 1, a mixture of methanol and methyl 2-methyl-2-(3-methyl-4-nitro-1H-pyrazol-1-yl)propanoate 3a (0.5 kg) was charged into an autoclave under nitrogen atmosphere, followed by slow addition of 10% (50% wet) Pd/C. Hydrogen was charged under pressure and the reaction mixture agitated at 25° C. until complete. The mixture was filtered, concentrated under reduced pressure and then slurried in MTBE for 2 h at 25° C. Filtration and drying under reduced pressure gave methyl 2-(4-amino-3-methyl-1H-pyrazol-1-yl)-2-methylpropanoate 10a (LC-MS, M+1=198).

Example 6 Preparation of methyl 2-(4-((4-chloro-5-(trifluoromethyl)pyrimidin-2-yl)amino)-3-methyl-1H-pyrazol-1-yl)-2-methylpropanoate 11a

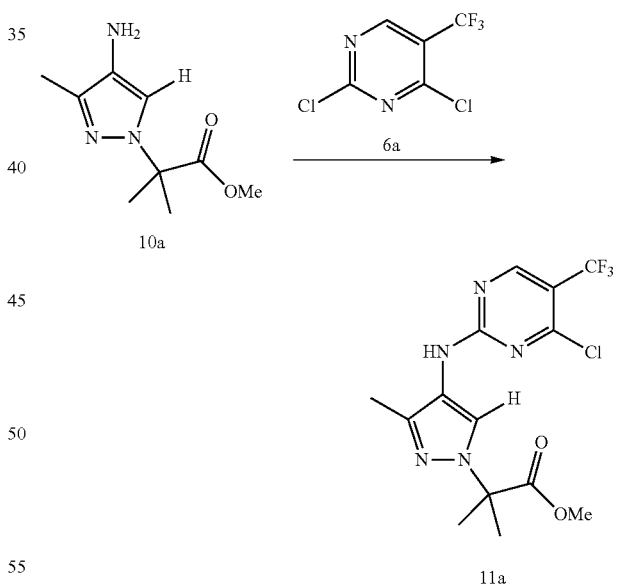

Following the procedure of Example 2, a mixture of methyl 2-(4-amino-3-methyl-1H-pyrazol-1-yl)-2-methylpropanoate 10a and DIPEA (1.2 equiv) in t-BuOH was warmed to 80° C. Then a solution of 2,4-dichloro-5-trifluoromethyl pyrimidine 6a in t-BuOH was added slowly drop wise at 80° C. After 15 minutes, LCMS showed the reaction was complete, including later eluting 59.9% of product ester 11a, earlier eluting 31.8% of undesired regioisomer (ester), and no starting material 10a. After completion of reaction, the mixture was cooled to room temperature and a solid was precipitated. The solid precipitate was filtered and dried to give methyl 2-(4-((4-chloro-5-(trifluoromethyl)pyrimidin-2-yl)amino)-3-methyl-1H-pyrazol-1-yl)-2-methylpropanoate 11a (LC-MS, M+1=378).

Although the foregoing has been described in some detail by way of illustration and example for purposes of clarity of understanding, the descriptions and examples should not be construed as limiting the scope of the present disclosure. Accordingly, all suitable modifications and equivalents may be considered to fall within the scope of the present disclosure as defined by the claims that follow. The disclosures of all patent and scientific literature cited herein are expressly incorporated in their entirety by reference.

What is claimed is:

1. A process for the preparation of a compound of formula I:

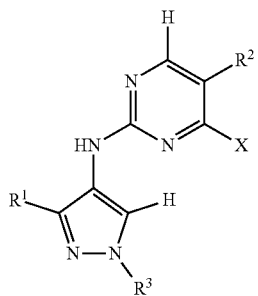

or a salt thereof, wherein:
X is chloro;
$R^1$ is $CH_3$;
$R^2$ is $CF_3$
$R^3$ is —$C(CH_3)_2C(O)NH_2$; and
the process comprising:
contacting a compound of formula II:

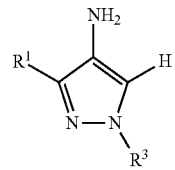

or a salt thereof, with a compound of formula III:

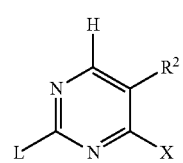

or a salt thereof, wherein L is chloro;
to form a compound of formula I or a salt thereof, wherein the method further comprising contacting a compound of formula II and a compound of formula III with a Lewis acid selected from $ZnCl_2$, $CuI/BF_3$ etherate, trimethylsilyl trifluoromethanesulfonate (TMSOTf), $TiCl_4$, $BiCl_3$, $InCl_3$, $BCl_3$, $Et_2Zn$, and $ZnBr_2$.

2. The process of claim 1, wherein the process further comprises purifying the compound of formula I or salt thereof, wherein the compound of formula I is refluxed in methanol, cooled, and filtered.

3. The process of claim 1 wherein the Lewis acid is zinc chloride.

4. The process of claim 1 wherein the compound of formula II and the Lewis acid $ZnCl_2$ are mixed in a solvent and the mixture is added to the compound of formula III.

5. The process of claim 1, further comprising purifying the compound of formula tor salt thereof formed.

6. The process of claim 1, further comprising contacting the compound of formula I with an excipient and processing the resulting composition into a capsule or tablet.

* * * * *

UNITED STATES PATENT AND TRADEMARK OFFICE
CERTIFICATE OF CORRECTION

PATENT NO. : 11,834,438 B2
APPLICATION NO. : 16/955717
DATED : December 5, 2023
INVENTOR(S) : Travis Remarchuk et al.

It is certified that error appears in the above-identified patent and that said Letters Patent is hereby corrected as shown below:

In the Claims

At Column 22, Claim 5, Line 40, replace "formula tor" with --formula I or--.

Signed and Sealed this
Fourth Day of June, 2024

Katherine Kelly Vidal
*Director of the United States Patent and Trademark Office*